United States Patent [19]

Leunissan

[11] 4,135,501
[45] Jan. 23, 1979

[54] DENTAL MASSAGE DEVICE

[76] Inventor: Henry P. Leunissan, 1811 Woodland Ave., Palo Alto, Calif. 94303

[21] Appl. No.: 793,749

[22] Filed: May 4, 1977

[51] Int. Cl.² .............................................. A61H 9/00
[52] U.S. Cl. .................................. 128/66; 128/62 A; 128/229; 285/8
[58] Field of Search ................ 128/66, 62 A, 229; 285/8

[56]  References Cited

U.S. PATENT DOCUMENTS

| 872,169 | 11/1907 | Clayton | 285/8 |
| 1,012,345 | 12/1911 | Ferguson | 285/8 |
| 2,208,031 | 7/1940 | Hooper | 128/229 |
| 3,271,053 | 9/1966 | Kurachi | 285/8 |
| 3,499,440 | 3/1970 | Gibbs | 128/66 |
| 3,590,813 | 7/1971 | Roszyk | 128/66 |

Primary Examiner—Lawrence W. Trapp

[57] ABSTRACT

A dental massage device comprising a nozzle portion having one of its ends open and provided with gripping members adapted to fit over and grip a conventional faucet aerator in a sealing relationship therewith. Its other end is provided with an aperture which is connected by flexible conduit means to an ejector which is operably connected to the flexible conduit.

5 Claims, 6 Drawing Figures

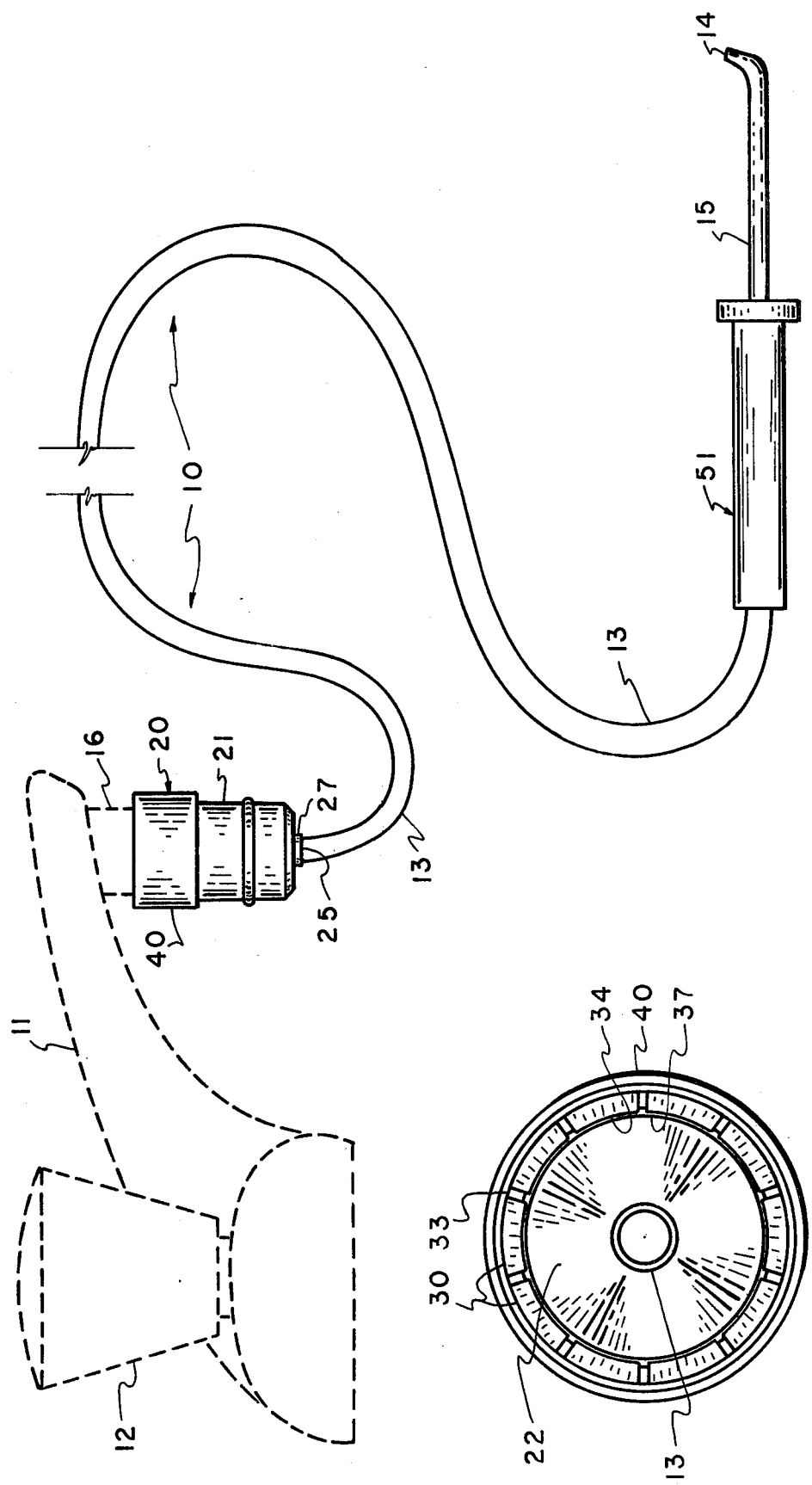

DENTAL MASSAGE DEVICE

BACKGROUND OF THE INVENTION

The present invention pertains to devices for cleaning teeth and massaging gums. More specifically, the present invention is concerned with a water jet apparatus whereby a stream of water is employed to clean the teeth and massage the gums.

Devices employing a jet of water for cleaning the teeth and massaging the gums are old and well known in the arts. However, such devices are characterized as being structurally complex and hence expensive to manufacture, or, are not readily adaptable for use with present day faucets equipped with aerator appurtanences. The present device overcomes these shortcomings of the prior art in the provision of a dental massage device which is relatively inexpensive to manufacture.

DESCRIPTION OF THE DRAWINGS

The above objects, together with other features and advantages of the instant invention will be apparent to one skilled in the art in light of the details of construction and operation of the present dental massage device as shown in the drawings and described in the ensuing detailed disclosure of its preferred embodiment which is particularly pointed out in the appended claims. In the drawing illustrating the preferred embodiment of the present invention, synonymous reference numerals are employed throughout in the various views to refer to identical components.

FIG. 1 in the drawings depicts an overall arrangement of the present device as shown installed on a conventional water outlet faucet.

FIG. 6 represents an end view of the adaptor assembly of FIG. 2 taken from its top end which connects to the water faucet.

DESCRIPTION OF THE PREFERRED EMBODIMENT(S)

Figure 3:
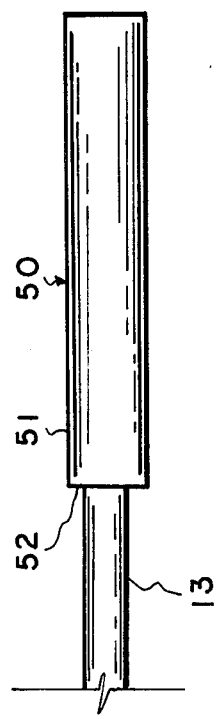
FIG. 3 illustrates a side elevation view of the water jet ejector handle connector of the present dental massage device.
Figure 2:
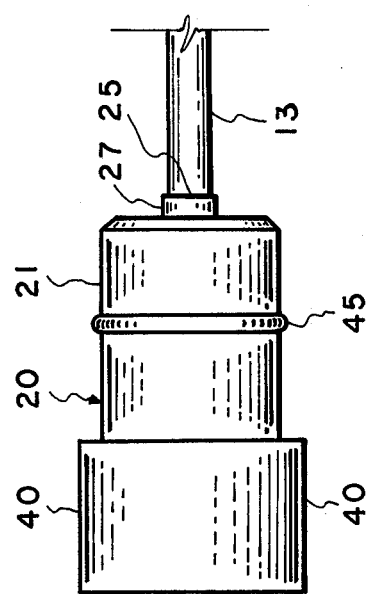
FIG. 2 in the drawings illustrates a side elevation view of the adaptor assembly of the present dental massage device.

FIG. 1 in the drawing depcits the basic manner in which the present dental massage device is employed. Specifically, the present device 10 is attached to the faucet 11 in the manner described below and upon manipulation of the handle 12 of the faucet assembly 11, water is caused to flow through the hose portion 13 where it exits from the tip 14 of the ejector 15. The user would mix the hot and cold water portions of the faucet assembly 11 such that the temperature of the water would feel comfortable in his mouth. The tip 14 of the ejector 15 would then be placed between the teeth or along the gums and the stream of temperature regulated water allowed to squirt between the teeth and/or along the gums from both sides, preferably mixing circular motion whereby any food particles between the teeth would be dislodged, while at the time massaging the gums. Such cleaning and treatment of the teeth and gums prevents infections, as well as cures infections and gum disease.

Referring both to FIG. 1 as well as 2 and 3 of the drawings, the present dental massage device 10 preferably comprises the adaptor or connecting member assembly 20. The assembly 20, as further shown in greater detail in the cross section view of FIG. 4, further comprises the main body portion 21 which is a cup shape cylindrical member defining the chamber portion 22, the member 21 being open at its end 23 for connection to and into which the faucet aerator member 16 bayonets in the fashion shown in FIG. 1 of the drawing.

The end portion 24 of the main body member 21 is provided with the centrally located hole or aperature 25 into which the end portion of the hose 13 fits. The portion 24 of the member 21 is drilled such that the hose 13 fits snuggly within the hole 25 and the hose 13 retained in the member 21 by virtue of the ferrule or retainer 26 which is lodged within the open end portion of the hole 13 a short distance from the end thereof. The member 26 can be any ring shaped member having an outside diameter slightly greater than the inside diameter of the hose 13 so as to expand its outer peripheral surface or make its outside diameter greater than the diameter of the hole 25 such that upon pulling the hose 13 into the position in FIG. 4, the hose is thereby restrained into position and cannot be easily pulled out of the member 21. In such fashion, the hose 13 is retained into the fixed position shown in FIG. 4 of the drawing such that when water pressure is applied within the adaptor 20, the hose 13 is accordingly retained in the position shown in the drawings. Moreover, the retainer 26 also prevents the user from accidentally pulling the hose 13 out of the adaptor 20. During use should such a strain be placed upon the member, the end portion 24 of the main body member 21 is provided with the elongated sleeve or extended portion 27 so as to promote the hose 13 to bend gradually as it exits from the hold 25 to avoid the hose 13 from being kinked sharply at the surface of the bottom portion 24 which would occur in the absence of the sleeve portion 27.

The main body member 21 further comprises the series of gripping portions 30, which as shown in FIG. 6, comprises 10 in number. FIG. 6 represents a preferred embodiment of the present invention, however, it can be appreciated that the number of gripping members 30 could vary as desired. Referring back to FIG. 4, the main body member 21 is slightly enlarged at its end 23 which defines the individual gripping members 30 so as to define the offset portion 31 which serves as a stop for the sleeve member 32 which functions as described below. The individual gripping portion 30 are preferably constructed integral with the main body portion 21 by merely slotting the end 23 thereof. This is accomplished by casting the main body portion 21 in a single piece and thereafter cutting the slot 33. It can be appreciated that where the gripping portions 30 are cast integral with the main body portion 21, then the latter must be constructed of a material whereby the individual gripping portion can be caused to flex. Accordingly, the thickness of the individual gripping 30 is made so as to provide the desired thickness of the individual gripping members 30.

Figure 4:
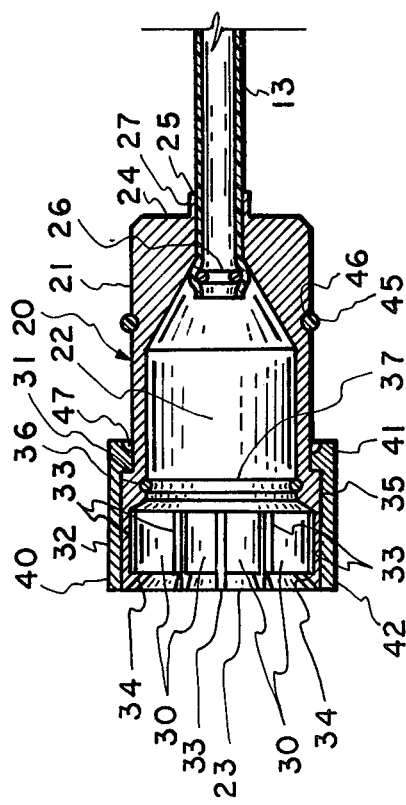
FIG. 4 represents a cross section view taken along the line A—A of FIG. 2.

As shown in FIG. 4, the individual gripping members 30 are provided with the offset or extended tooth portion 34 so as to provide a means of gripping the aerator member 16 as shown in FIG. 1. As an analogy, the assembly 20 is attached to and caused to grip the aerator 16 as would a conventional bottle cap would grip a bottle top, however, the present device being operably capable of repeated attachment and disengagement in the manner described below.

The inside diameter of the extended tooth portion 34 of the individual gripping portion 30 are made essentially equal to that of the conventional aerator 16, this dimension also being essentially equal to the inside diameter of the chamber 22 of the main body portion 21. The upper end portion 35 of the chamber 22 is provided with the groove 36 wherein the resilent O-ring shaped sealing member 37 is fitted. The seal 37 is provided for fitting around the outside peripheral surface of aerator 16 to thereby provide an essentially water tight relationship between the members. In such fashion, when the adaptor assembly 20 is fitted upon the aerator 16, water will be forced to accordingly flow through the main body portion 21, the hose 13 and exit through the ejector 15 via the exit tip 14.

The individual gripping portion 30 are caused to contract upon aerator 16 by virtue of the squeezing action of the sleeve member 40 which as shown in FIG. 4 of the drawings, is a tubular shaped member having its lower end portion 41 bored to receive the narrowed portion of the main body member 21. Conversely, the upper end portion 42 of the sleeve member 40 is bored to accommodate the expanded gripping end portion 23 of the main body member 21. As a preferred embodiment, the individual gripping member or retaining elements 30 are initially bent or sprung radially outwards whereby the faucet aerator 16 can be easily fitted therein the open end portion 23. The sleeve member 40 in turn is designed so as to impart a squeezing action upon the various flexible gripping members or elements by virtue of its inside diameter being essentially equal to the contracted diameter of the elements 30. By such structure, when the sleeve 40 is withdrawn from its position shown in FIG. 4, the individual gripping members 30 are allowed to be fully expanded or to be in their natural position at their farthest radial position taking with respect the longitudinal axis of the main body portion 21. Conversely, as shown in FIG. 4, the internal surface 44 defined within the end portion 42, that is, along its inner peripheral surface, thereby imparts a constricting or squeezing action upon the outer peripheral surfaces of the various gripping portion 30 to thereby cause them to move inwards and into contact with the outer peripheral surface of the aerator 16. In such manner, the adaptor assembly 20 is thereby operably attached to the aerator 16 in an essentially water-tight relationship by virtue of the gripping action of the gripping portions 30, the seal 37 sealing the aerator 16 within the nozzle assembly 20.

The main body portion 21 is provided with the sleeve stop member 45 which functions so as to prevent the sleeve 40 from slipping entirely off of the member 21. Preferably, the stop 45 comprises a conventional O-shaped resilient member which fits within the groove 46 provided essentially at the relative position shown in FIG. 4 so as to allow the sleeve 40 to be fully withdrawn from around the gripping members 30. The sleeve member 40 is provided with the circular shaped cut-out portion 47 to thereby accommodate the shape of the stop 45 which nestles therein when the sleeve 40 is butted there against.

Figure 5:
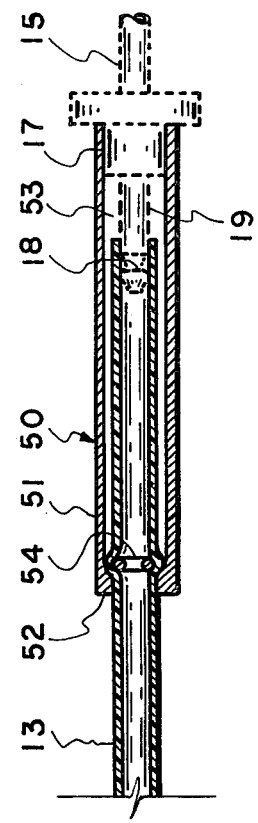
FIG. 5 represents a cross sectional view taken along the line B—B of FIG. 3.

As shown in FIGS. 1, 3 and 5 of the drawings, the water jet end of the present dental massage device comprises the handle assembly 50. The assembly 50 is further defined as comprising the elongated tubular main body portion 51 which is bored at its lower end 52 to receive the flexible hose member 13. Referring primarily to FIG. 5, the main body portion or handle portion 51 is bored at its end portion 52 to receive the flexible hose 13 snuggly, however, the majority of its length is bored or made of a greater diameter so as to provide the chamber 53 therein. The inside diameter of the chamber 53 is determined by the size of the restraining ferrel 54 which functions and serves the same purpose as the ferrule 26 with regard to the adaptor assembly 20. The length of the handle 51 is primarily determined in consideration of the convenience of the user. The extent that the hose 13 bayonets or fits there within is determined by the relative dimensions of the water jet member 15. The latter member is a conventional device available in the market today as replacements for use with various types of water jet dental massage and cleaning devices. Its connecting tip is provided with the expanded portion 17, the handle sleeve member 51 being bored to snuggly receive that circular portion therein which serves to frictionally grip the water jet 15 and hold it into position, together with the gripping action provided by virtue of the serrated or grooved portion 18 defined in the lower shaft portion 19 which is shoved within the open end of the flexible hose member 13. The hose number 13 is selected such that its inside diameter is slightly less than the outside diameter of the lower shaft portion 19 so as to realize an essentially water tight relationship between the members. Of course, an additional sealing means can be provided where the expanded portion 17 of the water jet assembly 15 bayonets within the open end portion of the handle member 51, viz., by an O-ring spanning the outer peripheral surface of the portion 17. It is to be appreciated that the water pressure applied to the various components of the present device would be no greater, and actually would be less, than that of the tap pressure emanating from the faucet assembly 11 since the present device is never actually shut off so as to provide any significant back pressure, but rather, only that defined by application of the tip 14 to the gums and teeth of the user. Therefore, it can be appreciated that the sealing pressures required within the present device need not be significant.

It will be apparent to one skilled in the art that various changes and modifications can be made within the ambit of the present invention without departing from its true scope and spirit. For example, the materials of construction can vary considerably, however, it is preferred to construct the members 20 and 50 out of a light weight plastic material which is somewhat resilient, e.g., with regard to the function of the gripping portions 30, and easily machinable. Suitable materials of construction would be nylon, polyvinyl chloride, and the like. The flexible hose member 13 can be made of any suitable resilient material, such as various different rubbers, vinyl compounds and the like. Moreover, the design of the gripping end portion 30 can vary considerably, for example, the members can be made individually and assembled together. The gripping elements 30 can be made to expand upon application and the sleeve 40 beveled along its inner peripheral surface so that it can be jammed over the outer peripheral surface of the gripping members 30 so as to constrict them and hold them into a gripping relationship with the aerator 16. Additionally, the flexible conduit 13 can be operably connected at either of its ends by other suitable conventional connecting means, e.g., by virtue of screwed fittings, snap-on connecting means, and the like. It is also intended that, within the scope of the present invention, the coupling itself can be employed for many different applications, such as to connect a portable dishwasher to a kitchen faucet. In other words, the hose 13 of the preferred embodiment could be removed and the coupling assembly could be made part of the hose assembly associated with the particular piece of equipment with which it is to be employed. In light of the above, it can be appreciated by one skilled in the art that many varying and different embodiments may be made within the scope of my inventive concept as disclosed herein, and accordingly, since many such modifications may be made in my embodiment as disclosed in detail herein in accordance with the descriptive requirements of the law, it is to be understood that the details of my inventive concept are to be interpreted as illustrative and not in a limiting sense. Therefore, what I intend to encompass within the ambit of my invention is that as set forth and particularly pointed out in the appended claims.

What I claim as invention is:

1. A dental massage device for coupling the cylindrical outflow end of a faucet to an elongated water ejector comprising:
    (a) an adaptor means including
        a generally cylindrical main body member provided with an axially formed chamber opening on a first end thereof and an axial bore extending from a second end thereof to open on said chamber, the peripheral surface of said main body member being provided with a plurality of longitudinally formed slots extending from said first end at least partially to said second end to thereby define a plurality of flexible gripping portions at said second end, each of said gripping portions being provided with a radially inwardly extending tooth means at its terminal end, and
        sleeve means disposed over said main body member and slidable along the outer peripheral surface thereof, said sleeve means being operative to squeeze said gripping members radially inwardly when it is positioned around said gripping members, causing said tooth means to grip the outer surface of said cylindrical outflow end and said sleeve means allows said gripping members to expand radially outwardly when it is not positioned therearound, releasing the grip of said tooth means on said outer surface of said cylindrical outflow end;
    (b) handle means including an elongated hollow member provided with a first axial bore extending from a first end towards a second end thereof and a second axial bore of a smaller diameter which extends from said second end towards said first end and which opens on said first axial bore, where an expanded portion of said water ejector can telescope into said first axial bore at said first end; and
    (c) flexible hose means including a tube having an external diameter less than said smaller diameter, the tube having a first end portion attached within the axial bore of said main body and having a second end portion disposed through said second bore and into said first bore, said flexible hose means further including a ferrule means inserted into said tube proximate said second end, said ferrule means having an outside diameter sufficient to expand the portion of the outer peripheral surface of said flexible hose which surrounds said ferrule to a diameter greater than said second diameter, thereby preventing the withdrawl of said tube from said handle means.

2. A dental massage device as recited in claim 1 wherein said tube extends to a depth within said hollow member sufficient such that its second end slips over and around in a sealing relationship with an end portion of an elongated water ejector that is telescoped into said hollow member.

3. A dental massage device as recited in claim 1 wherein said main body member is further defined in that said axial bore is of a diameter sufficient to receive said first end portion of said tube in a snug relationship; and said tube is rigidly affixed to said main body member by extending said second end of said tube into said cavity of said main body member and said flexible hose means further includes a second ferrule means fitted within said tube proximate said first end said ferrule means being of an outside diameter sufficient to expand the outside diameter of said tube when fitted therein to a diameter exceeding that of said axial bore of said main body member to thereby prevent withdrawl of said tube from said main body member.

4. A dental massage device as recited in claim 1 wherein said main body member is further defined in that it is provided with a flexible sealing member extending around the inner surface of said chamber so as to seal said main body member to the outer surface of said cylindrical outflow end when it is inserted thereupon; and
    said main body member is also further defined as being provided with an O-ring shaped member affixed to its outer peripheral surface so as to define a stop for said slidable sleeve means to thereby prevent its disengagement with said main body member.

5. An adaptor means for coupling the cylindrical outflow end of a faucet to a flexible hose means comprising
    a generally cylindrical main body member provided with an axially formed chamber opening on a first end thereof and an axial bore extending from a second end thereof to open on said chamber, said axial bore for receiving an end of said flexible hose means, the peripheral surface of said main body member being provided with a plurality of longitudinally formed slots extending from said first end at least partially to said second end to thereby define a plurality of flexible gripping portions at said second end, each of said gripping portions being provided with a radially inwardly extending tooth means at its terminal end, and
    sleeve means disposed over said main body member and slidable along the outer peripheral surface thereof, said sleeve means being operative to squeeze said gripping members radially inwardly when it is positioned around said gripping members, causing said tooth means to grip the outer surface of said cylindrical outflow end and said sleeve means allows said gripping members to expand radially outwardly when it is not positioned therearound, releasing the grip of said tooth means on said outer surface of said cylindrical outflow end.

* * * * *